United States Patent
Hirashima et al.

(10) Patent No.: US 6,471,984 B1
(45) Date of Patent: *Oct. 29, 2002

(54) CATAPLASM AND TAPE-AID CONTAINING A PLASTICIZER

(75) Inventors: Nobuchika Hirashima, Tosu (JP); Hideshi Oda, Tosu (JP); Daisuke Miyata, Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/694,477

(22) Filed: Oct. 24, 2000

Related U.S. Application Data

(63) Continuation of application No. 09/341,160, filed as application No. PCT/JP98/00121 on Jan. 14, 1998.

(51) Int. Cl.⁷ .......................... A61F 13/00; A61L 15/16; A61K 6/00
(52) U.S. Cl. ....................... 424/443; 424/447; 424/448; 424/449; 424/401
(58) Field of Search ................................. 424/443, 447, 424/448, 449

(56) References Cited

U.S. PATENT DOCUMENTS

| | | | | |
|---|---|---|---|---|
| 5,608,119 A | * | 3/1997 | Amano et al. | 568/676 |
| 5,725,874 A | * | 3/1998 | Oda et al. | 424/443 |

FOREIGN PATENT DOCUMENTS

| | | |
|---|---|---|
| JP | 58-88334 | 5/1983 |
| JP | 7-82200 | 3/1995 |
| JP | 8-104625 | 4/1996 |

* cited by examiner

*Primary Examiner*—Thurman K. Page
*Assistant Examiner*—Isis Ghali
(74) *Attorney, Agent, or Firm*—Kubovcik & Kubovcik

(57) ABSTRACT

A plasticizer consisting of 3-L-menthoxypropane-1,2-diol is excellent in plasticizing effect on a patch base and high in safety, stability and miscibility with the base. A patch containing the plasticizer is excellent in overall feeling such as adhesion and fit feeling to the skin and peeling pain.

9 Claims, No Drawings

CATAPLASM AND TAPE-AID CONTAINING A PLASTICIZER

This application is a continuation of application Ser. No. 09/341,160, filed Jul. 2, 1999, which is a 371 of PCT/JP98/00121 filed Jan. 14, 1998.

TECHNICAL FIELD

This invention relates to a plasticizer and a patch containing the plasticizer.

In particular, this invention relates to such a plasticizer that is excellent in plasticizing effect on a base for a patch, high in safety, stability and compatibility with the base, odorless and exhibits a refreshing effect, and also relates to a cataplasm (poultice) and a tape-aid (plaster) each containing the plasticizer.

BACKGROUND ART

Antiphlogistic and analgesic patches are generally used for lumbago, sprain, muscular pain, stiff shoulders, etc. from old times. However, those conventional patches still leave room for improvement in their overall feelings at the time of use, which include adhesion, stickiness and fitness (fit feeling) to the skin, pain caused on peeling, and odor. Further, in the case of a so-called systemic transdermal preparation which has often been used recently and make a medicine therein percutaneously absorbed to produce an intended therapeutic effect, it is indispensable to keep the preparation in contact with the skin for a long time. When a patch preparation is used for this purpose, the adhesion thereof to the skin is necessitated much more than usual because the therapeutic effect is greatly influenced by the area of the patched skin.

The feelings realized by the application of a patch to the skin, such as adhesion or fitness to the skin and pain caused by peeling off the patch, depend on the properties of the base of the patch. Generally, as the base becomes softer, it is improved in the adhesion and fitness and causes less pain upon peeling. Therefore, incorporating into a base an additive which plasticizes and softens the base is supposedly the simplest and surest method in order to easily improve the properties of the base without significantly changing the formulation to obtain the intended pharmaceutical characteristics.

However, at present, there is absolutely no such excellent plasticizer as to exhibit high compatibility with the base of the patch, plasticizing effect, high safety and excellent feelings of use such as smell.

Plasticizers now used for medicines include glycols such as propylene glycol and polyethylene glycol, some surfactants, fatty oils such as castor oil, and fatty acid esters typified by isopropyl myristate.

However, when these plasticizers are used for patches, fully satisfactory results cannot always be obtained for the following reasons: their plasticizing effects are insufficient for obtaining the intended pharmaceutical characteristics; these plasticizers have only low compatibility with the base to cause bleeding with time; the use thereof is limited because of their odor; decomposition or coloring is caused with time because of instability of the plasticizers; and unfavorable side effects are caused because the plasticizers irritate the skin.

An object of the present invention is to solve the above-described problems by providing a plasticizer capable of showing an excellent effect of plasticizing a base for a patch, and having high safety, stability and compatibility with the base. Another object of the present invention is to provide a patch, particularly, a cataplasm and a tape-aid, containing the plasticizer and having excellent overall feelings when in use such as adhesion and fitness to the skin and pain caused by peeling off the patch.

DISCLOSURE OF THE INVENTION

The above objects of this invention can be attained by using 3-L-menthoxypropane-1,2-diol as a plasticizer for the base of a patch.

The crux of this invention resides in a plasticizer composed of 3-L-menthoxypropane-1,2-diol, and in a patch, particularly a cataplasm and a tape-aid, containing the plasticizer in its base.

3-L-menthoxypropane-1,2-diol (which is also called 3-{(1R, 2S, 5R)-[5-methyl-2-(1-methylethyl) cyclohexyl]oxy}-1,2-propanediol) which is the plasticizer of this invention, is a known substance described in, e.g., Japanese Pat. Appln. Laid-Open Gazette No. Sho 58-88334 (88334/83) as a substance having a cooling or refreshing activity. Further, Japanese Pat. Appln. Laid-Open Gazette No. Sho 60-25908 (25908/85) discloses that this compound is useful as a cosmetic material, has an excellent cooling effect and is extremely safe for the skin. However, there has not been found any example of using said known substance as a plasticizer, to say nothing of an attempt to plasticize or soften the base for a patch by the use of this substance to obtain the desired pharmaceutical characteristics. Such an attempt has been made for the first time by the inventors of the present invention and the invention is based on this entirely new finding.

3-L-Menthoxypropane-1,2-diol is present in the forms of R- and S-optical isomers because it has an asymmetric carbon atom at the 2-position to which a hydroxyl group is attached. In the present invention, this compound may be used as a plasticizer in the form of racemic modification or singly in the R- or S-form obtained by resolution.

The base for the patch of this invention contains 3-L-menthoxypropane-1,2-diol in an amount of preferably 0.1 to 20% by weight, more preferably 0.5 to 10% by weight, of the total amount of the base. When the amount is less than 0.1% by weight, no sufficient effects as the plasticizer will be exhibited, while when it exceeds 20% by weight, no stable preparation will be prepared.

The drug to be used in the patch of this invention is not particularly limited but may be arbitrarily selected from among known conventional drugs. Such drugs include steroidal anti-inflammatory agents such as prednisolone, dexamethasone, hydrocortisone, fluocinolone acetonide, betamethasone valerate, betamethasone dipropionate, clobetasone butyrate and prednisolone succinate; nonsteroidal anti-inflammatory agents such as methyl salicylate, glycol salicylate, indomethacin, diclofenac, ibuprofen, ketoprofen, flufenamic acid, ketorolac, flurbiprofen, felbinac, suprofen, prarioprofen, tiaprofen, loxoprofen, tenidap, aspirin, actarit, mizoribine, oxaprozin, auranofin, indomethacin farnesyl, oxaprozin, mofezolac and etodolac, and their ester derivatives; antiallergic agents such as tranilast, azelastine, ketotifen, ibudilast, oxatomide, emedastine and epinastine; antihistamic agents such as diphenhydramine, chlorpheniramine, promethazine and tripelennamine; central nervous system stimulants such as chlorpromazine, nitrazepam, diazepam, phenobarbital and reserpine; hormones such as insulin, testosterone, norethisterone, methyltestosterone, progesterone and estradiol; antihypertensive agents such as clonidine, reserpine, guanethidine sulfate and efonidipine; cardiotonics such as digitoxin and digoxin; antiarrhythmic agents such as propranolol hydrochloride, procainamide hydrochloride, ajimalin, pindolol and tulobuterol hydrochloride; coronary vasodilators such as nitroglycerin, isosorbide dinitrate, papaverine hydrochloride and nifedipine; local anesthetics such as lidocaine, benzocaine, procaine hydrochloride and tetracaine; analgetic agents such as morphine, aspirin, codeine, acetanilide and aminopyrine; skeletal muscle relaxants such as eperisone, tizanidine, tolperisone and inaperisone; antifungal agents such as acetophenylamine, nitrofurazone, pentamycin, naphthiomate, miconazole, omoconazole, clotrimazole and butenafine hydrochloride; antineoplastic agents such as 5-fluorouracil, busulfan, actinomycin, bleomycin and mitomycin; investigational agents for urinary incontinence such as terodiline hydrochloride and oxybutynin hydrochloride; antiepileptics such as nitrazepam and meprobamate; antiparkinson agents such as chlorzoxazone and levodopa; assistants to the prohibition of smoking such as nicotine; vitamins and prostaglandins, though the drug usable in the patch is of course not limited to them. Further, those drugs may be used in the form of organic salt or inorganic salt.

The content of the drug is preferably 0.1 to 20% by weight, more preferably 0.5 to 10% by weight, of the total amount of the base for the patch, though it is not particularly limited.

The patch according to this invention may further contain various pharmacologically acceptable additives, so far as the object of the invention is not marred. Such additives include a stabilizer, an antioxidant, a perfume, a filler, an ultraviolet absorber, an antiseptic, an antimicrobial agent and a percutaneous absorbefacient.

Then, detailed description will be made of the cataplasm which is one of the patches according to this invention.

The cataplasm of this invention comprises in its base a plasticizer consisting of 3-L-menthoxy-propane-1,2-diol, a drug, a water-soluble polymer, a polyhydric alcohol and water.

As the base for the cataplasm of this invention, a hydrophilic base comprising a water-soluble polymer, a polyhydric alcohol and water is preferable in consideration of long-term stability, releasability and percutaneous absorbability of drug, and safety for the skin.

The water-soluble polymer to be used in the hydrophilic base may be one or more members suitably selected from the group consisting of gelatin, casein, pullulan, dextran, sodium alginate, soluble starch, carboxystarch, dextrin, carboxymethylc(ellulose, sodium carboxymethylcellulose, methylcellulose, ethylcellulose, hydroxyethylcellulose, polyvinyl alcohol, polyethylene oxide, polyacrylic acid, partially neutralized polyacrylic acid, polyacrylamide, polysodium acrylate, polyvinylpyrrolidone, carboxy-vinyl polymer, polyvinyl ether, methoxyethylene-maleic anhydride copolymer, isobutylene-maleic anhydride copolymer, N-vinylacetamide, copolymer comprising N-vinylacetamide and acrylic acid and/or acrylate salt and so forth. The content of the water-soluble polymer is preferably 1 to 30% by weight, more preferably 1 to 20% by weight, still more preferably 1 to 15% by weight, based on the total amount of the hydrophilic base. When the content is less than 1% by weight, the resulting base will have too low a viscosity to retain its shape, while when it exceeds 30% by weight, the resulting mixture of the constituents will have a high viscosity to lower the workability in preparing a homogeneous paste of the constituents or in applying the paste on a backing or the like.

The polyhydric alcohol is one or more members suitably selected from the group consisting of polyethylene glycol, propylene glycol, dipropylene glycol, polypropylene glycol, 1,3-butylene glycol, 1,4-butylene glycol, isobutylene glycol, glycerol, diglycerol, sorbitol and so forth. The content of the polyhydric alcohol is preferably 10 to 90% by weight, more preferably 10 to 70% by weight, still more preferably 20 to 60% by weight, based on the total amount of the hydrophilic base. When the content is less than 10% by weight, the resulting base will exhibit poor humectant effect, while when it exceeds 90% by weight, the solubility of the water-soluble polymer will be adversely affected.

The content of water is preferably 10 to 90% by weight, more preferably 20 to 80% by weight, based on the total amount of the hydrophilic base. The water is necessary in order to solubilize the water-soluble polymer to thereby make the resulting base develop its thickening, cohesive and shape-retaining properties.

If necessary, the hydrophilic base of the cataplasm may further contain one or more crosslinking agents in addition to the above essential components. The crossliking agents include polyvalent metal compounds such as aluminum hydroxide, aluminum chloride, calcium hydroxide, calcium chloride, aluminum sulfate, aluminum ammonium sulfate, aluminum potassium sulfate, magnesium aluminometasilicate and dihydroxyaluminum aminoacetate; and compounds each having at least two epoxy groups such as ethylene glycol diglycidyl ether, polyethylene glycol diglycidyl ether, propylene glycol diglycidyl ether, polypropylene glycol diglyidyl ether, polytetramethylene glycol diglycidyl ether, glycerol polyglycidyl ether, polyglycerol polyglycidyl ether, sorbitol polyglycidyl ether, sorbitan polyglycidyl ether, trimethylolpropane polyglycidyl ether, pentaerythritol polyglycidyl ether, resorcinol diglycidyl ether, neopentyl glycol diglycidyl ether and 1,6-hexanediol diglycidyl ether.

Further, the hydrophilic base of the cataplasm may contain one or more additives suitably selected from among fillers such as kaolin, zinc oxide, titanium dioxide, talc, bentonite and synthetic aluminum silicate; antiseptics such as thymol, methyl paraben, ethyl paraben and propyl paraben; antioxidants such as ascorbic acid, stearic esters, dibutylhydroxytoluene, butylhydroxyanisole, gallic esters, vitamin E, vitamin E acetate and disodium edetate; ultraviolet absorbers such as 2-hydroxy-4-methoxybenzophenone, ethyl p-aminobenzoatle, 2-(2-hydroxy-5-methylphenyl)benzotriazole, glycol salicylate, methyl salicylate and phenyl salicylate; and emulsifying agents such as fatty acid esters of sorbitan, fatty acid esters of glycerol, fatty acid esters of decaglycerol, fatty acid esters of polyoxyethylene sorbitan, fatty acid esters of polyethylene glycol and polyoxyethylene alkyl ethers.

It is essential that the support of the cataplasm of this invention be made of a material which has no influence on the release of a drug, i.e., that the support neither interact with nor adsorb a drug. The support is selected from the group consisting of films and sheets of polyethylene, polypropylene, polyvinyl chloride, polyester, nylon and polyurethane; porous materials, expanded materials and woven and nonwoven fabrics of these polymers; laminates each comprising one or more members selected from the group consisting of these films and sheets and one or more members selected from the group consisting of these materials and fabrics and so forth. The release sheet of the cataplasm according to this invention may be selected from the group consisting of films of polyethylene, polypropylenre and polyester; products of release treatment of these films with silicone compounds; release paper and so forth.

The preparation of the cataplasm of this invention will now be described, though the cataplasm can be easily prepared by known processes.

For example, a drug is solubilized in 3-L-menthoxypropane-1,2-diol to form a solution (A) which may, if necessary, be incorporated with one or more additives selected from the group consisting of a stabilizer, an antioxidant, an ultraviolet absorber, an emulsifying agent, an antiseptic, an antimicrobial and so forth. Separately, a water-soluble polymer is mixed into, dispersed and solubilized in a polyhydric alcohol and water to form a homogeneous paste (B). The solution (A) is added to the paste (B) to form a homogeneous dispersion. This dispersion is spread directly on a support, or alternatively it is once spread on a paper or film treated with a releasing agent and thereafter transferred to a support by pressing. Thus, a cataplasm according to this invention is prepared. The above-mentioned mixing order of base materials, a drug and other components is just one example, not limiting the mixing order for preparing the cataplasm according to this invention.

Next, detailed description will be made of the tape-aid which is one of the patches of this invention.

The tape-aid of this invention comprises in its base a plasticizer consisting of 3-L-menthoxy-propane-1,2-diol, a drug, a rosin ester derivative, either a styrene-isoprene-styrene block copolymer or an acrylic adhesive, and a softener.

Preferable proportions of these components are as follows: drug in an amount of 0.5 to 10% by weight, rosin ester derivative in 5 to 70% by weight, 3-L-menthoxypropane-1,2-diol in 0.5 to 10% by weight, styrene-isoprene-styrene block copolymer in 5 to 40% by weight and softening agent in 10 to 75% by weight, each percentage being based on the total amount of the base.

The tape-aid according to this invention comprises in its base, for example, (a) a nonsteroidal anti-inflammatory agent as the drug selected from the group consisting of diclofenac, ketoprofen, flurbiprofen, loxoprofen, ketorolac, felbinac, suprofen and ester derivatives and salts of these drugs, (b) a plasticizer comprising 3-L-menthoxypropane-1,2-diol, (c) a rosin ester derivative, (d) a styrene-isoprene-styrene block copolymer or an acrylic adhesive as the base polymer and (e) a softening agent, and a known base material for tape-aid if necessary.

The support for the tape-aid is selected from among polypropyene fabrics and polyester fabrics which have no influence on the release of a nonsteroidal anti-inflammatory agent. The polyester fabric is preferably one made of polyethylene terephthalate (PET) or polybutylene terephthalate (PBT). In order to attain excellent release of a nonsteroidal anti-inflammatory agent, it is essential that the support not interact with a nonsteroidal anti-inflammatory agent, i.e., not adsorb it. From this standpoint, the optimum polymer constituting the support is polypropylene, PET or PBT. The use of a support made of polypropylene, PET or PBT prevents the adsorption of a drug to the support to enable excellent release of the drug.

The tape-aid according to this invention is desirably provided with such stretchability that the average stresses at 50% elongation in lengthwise and widthwise directions are each 0.3 kg/cm or below, so that it can be applied also to a bend of human body. By virtue of this stretchability, the tape-aid according to this invention is capable not only of being used expediently but also of following the move of the skin so that the friction and pressure during the use of the tape-aid on the skin are decreased, thus causing little side effects such as contact dermatitis.

The rosin ester derivative is a resin which is used for the purpose of providing the resulting tape-aid with adhesion. The derivative is the product prepared by esterifying various rosins and subjecting the obtained esters to hydrogenation or purification. The esters include methyl ester, glycerol ester and pentaerythritol ester. The rosin ester derivatives include Ester Gum A, AA-G, H and HP (trade names, products of Arakawa Chemical Industry (Co, LTD.), Hariester-L, S and P (trade names, products of Harima Chemicals, Inc.), Super Ester A-75 (trade name, a product of Arakawa Chemical Industry Co., Ltd.), KE-311 (trade name, a product of Arakawa Chemical Industry Co., Ltd.), Hercolyn D (trade name, a product of Hercules Inc.) and Foral 85 and 105 (trade names, products of Hercules Inc.).

The base polymer of the tape-aid may be suitably selected from conventional ones in consideration of safety for the skin, releasability of a drug and adhesion to the skin; for example, from the standpoint of the release characteristics of a nonsteroidal anti-inflammatory agent, it is preferable that the base polymer be a styrene-isoprene-styrene block copolymer having a particularly low polarity. Such block copolymers include Cariflex TR-1107, TR-1111, TR-1112 and TR-1117 (trade names, products of Shell chemical) and Solprene 428 (trade name, a product of Phillips Petroleum). These styrene-isoprene-styrene block copolymers may be each used together with other polymer such as polyisobutylene. Vistanex (trade name, a product of Exxon Kagaku) is preferably used as the polyisobutylene.

The acrylic adhesive includes as a preferable example a polymer based on an alkyl (meth)acrylate. The polymer may be a copolymer of an alkyl (meth) acrylate and a compound polymerizable with the (meth)acrylate, such as a functional monomer, multifunctional monomer or vinyl compound. Preferable acrylic adhesive includes NISSETSU PE-300 (tradename, mfd. by Nippon Carbide Industries Co., Ltd.).

The softening agent serves to plasticize or soften the styrene-isoprene-styrene block copolymer used as the base polymer to keep the adhesion of the resulting tape-aid to the skin at a proper level. The softening agent may be selected from the group consisting of almond oil, olive oil, camellia oil, persic oil, peanut oil, liquid paraffin and so forth. The content of the softening agent is preferably 150 to 350 parts by weight per 100 part by weight of the styrene-isoprene-styrene block copolymer.

The content of a drug is preferably 70 to 1200 $\mu g/cm^2$ of the base from the standpoints of therapeutically effective amount or a drug to be released and availability thereof, though it is not particularly limited.

The tape-aid according to this invention can be easily prepared by known processes. For example, it can be prepared by mixing a styrene-isoprene-styrene block copolymer with a softening agent and a rosin ester derivative under heating at 120 to 160° C. by the use of a mixing machine such as kneader or mixer, adding a drug and 3-L-menthoxypropane-1,2-diol to the obtained mixture, and applying the resulting mixture to a support either by spreading the mixture directly on a woven- or nonwoven-fabric support of polypropylene or polyester or by once spreading the mixture on a paper or film treated with a releasing agent and thereafter covering the spread mixture with a desired support and then transferring the mixture to the support by pressing.

BEST MODE FOR CARRYING OUT THE INVENTION

This invention will be illustrated in greater detail with the following Examples etc. wherein wt. % is based on the total amount of the base. The Examples though should not be construed as limiting the invention.

EXAMPLE 1

Cataplasm

| (A) | 3-L-menthoxypropane-1,2-diol | 1.0% by weight |
|---|---|---|
|  | diclofenac | 0.5% by weight |
| (B) | purified water | 48.5% by weight |
|  | gelatin | 8.0% by weight |
|  | kaolin | 1.0% by weight |
|  | glycerol | 35.0% by weight |
|  | polysodium acrylate | 2.0% by weight |
|  | polyvinyl alcohol | 3.0% by weight |
|  | aluminum hydroxide | 1.0% by weight |

The above ingredients were solubilized together and agitated to obtain a homogeneous paste. The paste was applied on a polypropylene nonwoven fabric with a spreader to obtain a preparation layer having a thickness of 1 mm. Then, the preparation layer was covered with a polypropylene film and cut into pieces each having a predetermined size to obtain intended cataplasms.

EXAMPLE 2

Cataplasm

| (A) | 3-L-menthoxypropane-1,2-diol | 2.0% by weight |
|---|---|---|
|  | loxoprofen | 1.0% by weight |
|  | thymol | 0.1% by weight |
| (B) | purified water | 62.4% by weight |
|  | gelatin | 3.0% by weight |
|  | titanium oxide | 1.0% by weight |
|  | glycerol | 25.0% by weight |
|  | polysodium acrylate | 3.0% by weight |
|  | carboxymethyl cellulose | 1.0% by weight |
|  | ethylene glycol diglycidyl ether | 1.0% by weight |
|  | sorbitan fatty acid ester | 0.5% by weight |

The above ingredients were solubilized together and agitated to obtain a homogeneous paste. The paste was applied on a polyester nonwoven fabric with a spreader to obtain a preparation layer with a thickness of 0.5 mm. Then, the preparation layer was covered with a polyethylene film and cut into pieces of a predetermined size to obtain intended cataplasms.

EXAMPLE 3

Cataplasm

| (A) | (2S)-3-L-menthoxypropane-1,2-diol | 3.0% by weight |
|---|---|---|
|  | clobetasone butyrate | 0.5% by weight |
|  | ethyl paraben | 0.2% by weight |
| (B) | purified water | 42.3% by weight |
|  | methoxyethylene-anhydrous maleic acid copolymer | 5.0% by weight |
|  | synthetic aluminium silicate | 3.0% by weight |
|  | glycerol | 40.0% by weight |
|  | polyacrylic acid | 2.0% by weight |
|  | polyvinyl alcohol | 2.5% by weight |
|  | calcium hydroxide | 1.5% by weight |

The above ingredients were solubilized together and agitated to obtain a homogeneous paste. The paste was applied on a polyurethane film with a spreader to obtain a preparation layer with a thickness of 1 mm. Then, the preparation layer was covered with a polyester film and cut into pieces of a predetermined size to obtain intended cataplasms.

EXAMPLE 4

Cataplasm

| (A) | 3-L-menthoxypropane-1,2-diol | 5.0% by weight |
|---|---|---|
|  | keroprofen | 0.5% by weight |
| (B) | purified water | 36.0% by weight |
|  | N-vinylacetamide | 5.0% by weight |
|  | glycerol | 47.0% by weight |
|  | polyacrylic acid | 3.0% by weight |
|  | carboxymethyl cellulose | 1.0% by weight |
|  | magnesium metasilicate alminate | 1.5% by weight |
|  | glycerol fatty acid ester | 1.0% by weight |

The above ingredients were solubilized together and agitated to obtain a homogeneous paste. The paste was applied on a polyester nonwoven fabric with a spreader to obtain a preparation layer having a thickness of 1 mm. Then, the preparation layer was covered with a polyester film and cut into pieces of a predetermined size to obtain intended cataplasms.

EXAMPLE 5

Cataplasm

The procedure of Example 2 was followed except that the content of 3-L-menthoxypropane-1,2-diol was reduced to 0.05 wt. % and the balance was made up with purified water, thereby preparing cataplasms.

EXAMPLE 6

Cataplasm

The procedure of Example 2 was followed except that the Content of 3-L-menthoxypropane-1,2-diol was increased to 22 wt. % and the purified water was reduced by the amount of the diol increased, thereby preparing cataplasms.

EXAMPLE 7

Tape-aid

| styrene-isoprene-styrene block copolymer | 22.5% by weight |
|---|---|
| polyisobutylene | 5.0% by weight |
| tackifier (rosin ester) | 15.0% by weight |
| liquid paraffin | 52.0% by weight |

| | |
|---|---|
| 3-L-methoxypropane-1,2-diol | 5.0% by weight |
| ketotifen | 0.5% by weight |

The above components were agitated under heating, thereby obtaining a paste. The paste was spread on a support to obtain a desired tape-aid containing ketotifen.

EXAMPLE 8

Tape-aid

| | |
|---|---|
| styrene-isoprene-styrene block copolymer (trade name: Cariflex TR-1107) | 20.0% by weight |
| liquid paraffin | 43.5% by weight |
| polyisobutylene (trade name: Vistanex) | 10.0% by weight |
| rosin ester derivative (trade name: KE-311) | 21.5% by weight |
| 3-L-menthoxypropane-1,2-diol | 4.0% by weight |
| diclofenac | 1.0% by weight |

The above components were mixed by a mixer to obtain a paste. The paste was applied on a plastic film previously endowed with releasability, and then covered with a PBT nonwoven fabric and pressure-contact transferred to obtain a desired tape-aid.

EXAMPLE 9

Tape-aid

| | |
|---|---|
| styrene-isoprene-styrene block copolymer (trade name: Cariflex TR-1111) | 16.0% by weight |
| liquid paraffin | 23.0% by weight |
| polyisobutylene (trade name: Vistanex) | 8.0% by weight |
| rosin ester derivative (trade name: Ester Gum H) | 40.0% by weight |
| (2S)-3-L-menthoxypropane-1,2-diol | 10.0% by weight |
| ketoprofen | 3.0% by weight |

The above components were mixed together by a kneader to obtain a paste. The paste was applied on a plastic film previously endowed with releasability, thereon covered with a polypropylene nonwoven fabric and pressure-contact transferred to obtain a desired tape-aid.

EXAMPLE 10

Tape-aid

The procedure of Example 8 was followed except that the content of 3-L-menthoxypropane-1,2-diol was reduced to 0.05 wt. % and the balance was made up with liquid paraffin, thereby producing a tape-aid.

EXAMPLE 11

Tape-aid

The procedure of Example 8 was followed except that the content of 3-L-menthoxypropane-1,2-diol was increased to 21 wt. % and the liquid paraffin was reduced by the amount of the diol increased, thereby producing a tape-aid.

COMPARATIVE EXAMPLE 1

Cataplasm

The procedure of Example 4 was followed except that the 3-L-menthoxypropane-1,2-diol was replaced with purified water, thereby producing cataplasms.

COMPARATIVE EXAMPLE 2

Cataplasm

The procedure of Example 4 was followed except that the 3-L-menthoxypropane-1,2-diol was replaced with isopropyl myristate, thereby producing cataplasms.

COMPARATIVE EXAMPLE 3

Cataplasm

The procedure of Example 4 was followed except that the 3-L-menthoxypropane-1,2-diol was replaced with triacetin, thereby producing cataplasms.

COMPARATIVE EXAMPLE 4

Cataplasm

The procedure of Example 4 was followed except that the 3-L-menthoxypropane-1,2-diol was replaced with macrogol 400, thereby producing cataplasms.

COMPARATIVE EXAMPLE 5

Cataplasm

The procedure of Example 4 was followed except that the 3-L-menthoxypropane-1,2-diol was replaced with propylene glycol, thereby producing cataplasms.

COMPARATIVE EXAMPLE 6

Cataplasm

The procedure of Example 4 was followed except that the 3-L-menthoxypropane-1,2-diol was replaced with castor oil, thereby producing cataplasms.

COMPARATIVE EXAMPLE 7

Cataplasm

The procedure of Example 4 was followed except that the 3-L-menthoxypropane-1,2-diol was replaced with glycerin monostearate, thereby producing cataplasms.

TEST EXAMPLE 1

The cataplasms of Examples 2, 5 and 6 were each measured with a viscotester for the viscosity of their plaster (base) at the time of spreading the base on their own support to evaluate the spreadability of the plaster and further the adhesion, stickiness and stability with the lapse of time (exudation) of the plaster after being cured and stabilized. The results are given in Table 1.

TABLE 1

|  | Viscosity (poise) | Spreadability | Adhesion | Stickiness | Exudation |
|---|---|---|---|---|---|
| Ex. 2 | 32,000 | ○ | ○ | ○ | ○ |
| Ex. 5 | 45,000 | Δ | X | ○ | ○ |
| Ex. 6 | 21,000 | X | Δ | X | X |

○; good
Δ; a little no good
X; no good

It is apparent from the results given above that the plaster (base) of the cataplasm of Example 2, which contained 3-L-menthoxypropane-1,2-diol in an optimum concentration (2% by weight), exhibited a proper viscosity when being spread and also exhibited good results in all of the other items. On the other hand, in Examples 5 and 6 wherein the concentration of the diol was outside an optimum range of 0.1 to 20% by weight, the obtained cataplasms were unsatisfactory as compared with that of Example 2. These results prove that the optimum concentration of 3-L-menthoxypropane-1,2-diol in a cataplasm is 0.1 to 20% by weight based on the whole base.

TEST EXAMPLE 2

The tape-aids of Examples 8, 10 and 11 were each measured with a viscotester for the viscosity of their plaster (base) at the time of spreading the base on their own support in the same manner as that of Test Example 1 to evaluate the spreadability of the plaster and further the adhesion, stickiness and stability with the lapse of time [tonguing out: flowing out of part of the plaster (base) from between the support and the base] of the plaster after being cured and stabilized. The results are given in Table 2.

TABLE 2

|  | Viscosity (poise) | Spreadability | Adhesion | Stickiness | Tonguing |
|---|---|---|---|---|---|
| Ex. 8 | 29,000 | ○ | ○ | ○ | ○ |
| Ex. 10 | 41,000 | Δ | X | ○ | ○ |
| Ex. 11 | 19,000 | X | ○ | X | X |

○; good
Δ; a little no good
X; no good

It is apparent from the results given above that the plaster (base) of the tape-aid of Example 8, which contained 3-L-menthoxypropane-1,2-diol in an optimum concentration (4% by weight), exhibited a proper viscosity when being spread and also exhibited good results in all of the other items. On the other hand, in Examples 10 and 11 wherein the concentration of the diol was outside an optimum range of 0.1 to 20% by weight, the obtained tape-aids were unsatisfactory as compared with that of Example 8. These results prove that the optimum concentration of 3-L-menthoxypropane-1,2-diol in a tape-aid is 0.1 to 20% by weight based on the whole base.

TEST EXAMPLE 3

Determination of Gel Strength and Organoleptic Test

Only the prepared plaster (base) of each of the cataplasms of Example 4 and Comparative Examples 1 to 7 was packed in a hermetically closed vessel, and taken out after being cured and stabilized to determine the gel strength of the base with a rheometer. At the same time, each cataplasm was evaluated for overall feeling realized by the use thereof (which includes adhesion, fitness and stickiness to the skin, bleeding of the plasticizer, smell, remains of the plaster, and pain caused on peeling) by organoleptic tests. Each cataplasm was applied to the elbow for four hours. The results are given in Table 3.

TABLE 3

|  | Gel Strength (g) | Adhesion | Fit Feeling | Stickiness | Bleeding | Odor | Plaster Remains | Peeling Pain |
|---|---|---|---|---|---|---|---|---|
| Ex. 4 | 173 | ⊙ | ⊙ | ○ | ○ | ○ | ○ | ⊙ |
| Comp. Ex. 1 | 225 | ○ | ○ | ○ | ○ | ○ | ○ | ○ |
| Comp. Ex. 2 | 169 | ○ | ○ | Δ | X | ○ | Δ | ○ |
| Comp. Ex. 3 | 188 | ○ | ○ | Δ | X | ○ | ○ | ○ |
| Comp. Ex. 4 | 220 | ○ | Δ | X | ○ | ○ | ○ | Δ |
| Comp. Ex. 5 | 170 | ⊙ | ○ | X | Δ | ○ | Δ | Δ |
| Comp. Ex. 6 | 175 | Δ | ○ | X | X | Δ | Δ | ○ |
| Comp. Ex. 7 | 208 | ○ | ○ | Δ | X | ○ | ○ | ○ |

⊙: better than conventional ones
○; as good as conventional ones
Δ; worse than conventional ones
X; no good It is apparent from the results given above that the plaster (base) of Example 4 containing 3-L-menthoxypropane-1,2-diol was very lowered in gel strength and was plasticized and softened as compared with that of Comparative Example 1 containing no plasticizer.

The plasters (bases) of Comparative Examples 2 to 7 were also lowered in gel strength, however, scarcely improved in the adhesion and fitness to the skin. Even Comparative Example 5 which was only improved in adhesion was rather inferior to conventional products in the overall feeling when in use such as bleeding (compatibility of the plasticizer with the base), stickiness, and remains of the plaster.

On the other hand, the cataplasm of Example 4 containing 3-L-menthoxypropane-1,2-diol was superior to the conventional products in adhesion and fitness to the skin, and pain when peeling. Thus, the cataplasm of Example 4 had the intended characteristics, which proves the utility of 3-L-menthoxypropane-1,2-diol as the plasticizer for the base of a cataplasm.

TEST EXAMPLE 4

Test on Safety for the Skin

The cataplasms of Examples 1 to 4 and Comparative Examples 2 to 3 were examiner for safety for the skin.

The safety of each cataplasm for the skin was determined by 30 healthy male and female subjects according to the 48-hour closed patch test. The change in the skin of each subject was observed 1 and 24 hours after the peeling of the cataplasm to evaluate the irritativeness of the cataplasm to the skin according to the following criteria. The results are given in Tables 4 and 5. Subjects scored ± or more (±, + or ++) were regarded as positive.

−: no change in the skin
±: slight rubefaction
+: clear rubefaction
++: heavy contact dermatitis

TABLE 4

Lapse of time after peeling off poultice: 1 hour

| Samples | Number of Subjects | | | | Percentage of Positive Reaction (%) |
|---------|----|---|---|----|---------|
|         | ++ | + | ± | −  | (± or more) |
| Ex. 1   | 0  | 0 | 0 | 30 | 0.0 |
| Ex. 2   | 0  | 0 | 1 | 29 | 3.3 |
| Ex. 3   | 0  | 0 | 0 | 30 | 0.0 |
| Ex. 4   | 0  | 0 | 1 | 29 | 3.3 |
| Comp. Ex. 2 | 0 | 0 | 5 | 25 | 16.7 |
| Comp. Ex. 3 | 0 | 1 | 3 | 26 | 13.3 |

TABLE 5

Lapse of time after peeling off poultice: 24 hours

| Samples | Number of Subjects | | | | Percentage of Positive Reaction (%) |
|---------|----|---|---|----|---------|
|         | ++ | + | ± | −  | (± or more) |
| Ex. 1   | 0  | 0 | 0 | 30 | 0.0 |
| Ex. 2   | 0  | 0 | 0 | 30 | 0.0 |
| Ex. 3   | 0  | 0 | 0 | 30 | 0.0 |
| Ex. 4   | 0  | 0 | 0 | 30 | 0.0 |
| Comp. Ex. 2 | 0 | 0 | 2 | 28 | 6.7 |
| Comp. Ex. 3 | 0 | 0 | 3 | 27 | 10.0 |

The above results show that the cataplasms of Examples 1 to 4 of this invention are extremely high in safety for the skin.

INDUSTRIAL APPLICABILITY

According to the present invention, 3-L-menthoxypropane-1,2-diol which has been known as a refrigerant is contained as a plasticizer in the base of a patch. As a result, the diol exhibits excellent plasticizing effect on the patch base and is high in safety, stability and compatibility with the base. Therefore, when the patch containing the diol is applied to the skin, the patch exhibits improved overall feelings such as adhesion and fitness to the skin, and pain when peeling. Further, such a patch does not cause skin irritation such as contact dermatitis even when applied and peeled repeatedly, and is thus highly safe. Furthermore, the patch is odorless and serves comfortable refreshing refrigeration to the skin.

Therefore, the plasticizer and patch of this invention are suited for use in medical products, thus having high industrial applicability.

What is claimed is:

1. A cataplasm comprising a base on a support, said base having a viscosity within a range of from more than 21,000 to 45,000 poise and comprising a plasticizer consisting of 3-L-menthoxypropane-1,2-diol, a drug in an amount of 70 to 1200 μg/cm² of the base, a water-soluble polymer, a polyhydric alcohol and water.

2. A tape-aid comprising a base on a support, said base having a viscosity within a range of from more than 19,000 to 41,000 poise and comprising a plasticizer consisting of 3-L-menthoxypropane-1,2-diol, a drug in an amount of 70 to 1200 μg/cm² of the base, a rosin ester derivative, either a styrene-isoprene-styrene block copolymer or an acrylic adhesive, and a softener.

3. The cataplasm according to claim 1, wherein said viscosity ranges from 32,000 to 45,000.

4. The tape-aid according to claim 2, wherein said viscosity ranges from 29,000 to 41,000.

5. The cataplasm according to claim 1, wherein said water-soluble polymer is at least one member selected from the group consisting of gelatin, casein, pullulan, dextran, sodium alginate, soluble starch, carboxystarch, dextrin, carboxymethylcellulose, sodium carboxymethylcellulose, methyl cellulose, ethyl cellulose, hydroxyethylcellulose, polyvinyl alcohol, polyethylene oxide, polyacrylic acid, partially neutralized polyacrylic acid, polyacrylicamide, polysodium acrylate, polyvinylpyrrolidone, carboxyvinyl polymer, polyvinyl ether, methoxyethylene-maleic anhydride copolymer, isobutylene-maleic anhydride copolymer, N-vinylacetamide, copolymer comprising N-vinylacetamide and acrylic acid and/or acrylate salt.

6. The cataplasm according to claim 1, wherein said polyhydric alcohol is at least one member selected from the group consisting of polyethylene glycol, propylene glycol, dipropylene glycol, polypropylene glycol, 1,3-butylene glycol, 1,4-butylene glycol, isobutylene glycol, glycerol, diglycerol and sorbitol.

7. The cataplasm according to claim 1, wherein the base comprises 0.1 to 20% by weight of 3-L-menthoxypropane-1,2-diol, 1 to 30% by weight of the water-soluble polymer, 10 to 70% by weight of the polyhydric alcohol and 20 to 80% by weight of water, based on the total amount of the base.

8. The tape-aid according to claim 2, wherein the softener is at least one member selected from the group consisting of almond oil, olive oil, camellia oil, persic oil, peanut oil, liquid paraffin.

9. The tape-aid according to claim 2, wherein the base comprises the rosin ester derivative in 5 to 70% by weight, 3-L-menthoxypropane-1,2-diol in 0.5 to 10% by weight, the styrene-isoprene-styrene block copolymer in 5 to 40% by weight and the softener in 10 to 75% by weight, based on the total amount of the base.

* * * * *